United States Patent [19]

Shimada et al.

[11] Patent Number: 5,214,048

[45] Date of Patent: May 25, 1993

[54] OXETANOCINS

[75] Inventors: Nobuyoshi Shimada, Tokyo; Shigeru Hasegawa, Yono; Takayuki Tomizawa, Machida; Seiichi Saito, Kashiwa; Kyoichi Shibuya, Urawa; Akio Fujii, Kamakura; Hiroo Hoshino, Maebashi; Kenichi Matsubara, Suita; Takemitsu Nagahata, Toyonaka; Katsutoshi Takahashi, Tokyo; Yukihiro Nishiyama, Aichi, all of Japan

[73] Assignee: Nippon Kayaku Kabushiki Kaisha, Tokyo, Japan

[21] Appl. No.: 439,270

[22] Filed: Nov. 20, 1989

Related U.S. Application Data

[63] Continuation-in-part of Ser. No. 07/194,419, May 13, 1988, abandoned.

[30] Foreign Application Priority Data

| May 19, 1987 | [JP] | Japan | 62-120159 |
| Oct. 30, 1987 | [JP] | Japan | 62-273266 |
| Dec. 11, 1987 | [JP] | Japan | 62-312280 |

[51] Int. Cl.$^5$ .............. A61K 31/52; C07D 473/34; C07D 473/18; C07D 473/30
[52] U.S. Cl. ........................... 514/262; 435/88; 514/265; 514/266; 544/264; 544/265; 544/276; 544/277
[58] Field of Search ............... 544/277, 276, 264, 265; 514/267, 266; 435/88

[56] References Cited

U.S. PATENT DOCUMENTS

| 2,928,773 | 3/1960 | Klein | 435/88 |
| 4,460,765 | 7/1984 | Naito et al. | 536/26 |
| 4,543,255 | 9/1985 | Shealy et al. | 514/258 |
| 4,617,304 | 10/1986 | Ashton et al. | 514/261 |
| 4,634,706 | 1/1987 | Kaneko et al. | 514/262 |
| 4,728,736 | 3/1988 | Shealy et al. | 544/254 |
| 4,742,064 | 5/1988 | Vince | 514/258 |
| 4,743,689 | 5/1988 | Shimada et al. | 544/277 |
| 4,845,215 | 7/1989 | Shimada | 544/267 |

(List continued on next page.)

FOREIGN PATENT DOCUMENTS

| 0098186 | 1/1984 | European Pat. Off. . |
| 0182315 | 11/1985 | European Pat. Off. . |
| 0217580 | 4/1987 | European Pat. Off. . |

(List continued on next page.)

OTHER PUBLICATIONS

Antiviral Research, vol. 13, No. 1, Jan. 1990, pp. 41-52, Elsevier Science Publishers B.V. (Biomedical Division): A. K. Field, et al.

(List continued on next page.)

Primary Examiner—Cecilia Tsang
Attorney, Agent, or Firm—Nields & Lemack

[57] ABSTRACT

This invention relates to novel oxetanocins represented by the following general formula (I):

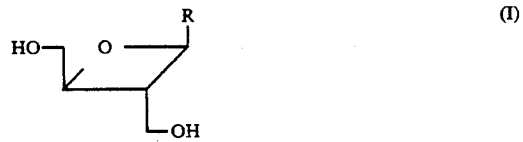

wherein R represents a group represented by

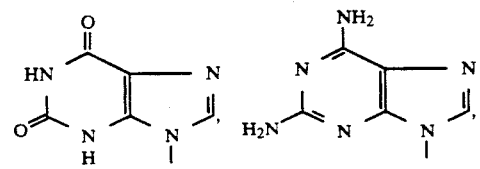

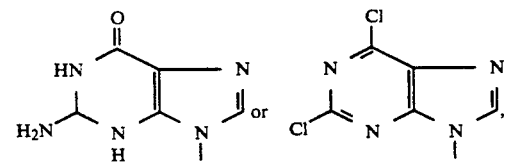

and their pharmacologically acceptable salts which have antiviral activities.

7 Claims, No Drawings

U.S. PATENT DOCUMENTS

| | | | |
|---|---|---|---|
| 4,892,876 | 1/1990 | Hoshino | 514/265 |
| 4,960,910 | 10/1990 | Kato | 549/510 |
| 4,992,368 | 2/1991 | Saito | 544/265 |
| 5,028,598 | 7/1991 | Kurabayashi | 544/184 |
| 5,041,447 | 8/1991 | Saito | 514/262 |

FOREIGN PATENT DOCUMENTS

| | | | |
|---|---|---|---|
| 0285432 | 10/1988 | European Pat. Off. . | |
| 0291917 | 11/1988 | European Pat. Off. . | |
| 0322854 | 7/1989 | European Pat. Off. . | |
| 0334250 | 9/1989 | European Pat. Off. . | |
| 0366059 | 2/1990 | European Pat. Off. . | |
| 0358154 | 3/1990 | European Pat. Off. . | |
| 0009696 | 1/1983 | Japan | 435/88 |
| 0208295 | 9/1987 | Japan . | |
| 0303993 | 12/1988 | Japan | 544/264 |
| 3-504728 | 10/1991 | Japan . | |

OTHER PUBLICATIONS

Tetrahedron Letters, 29, 4739–4742, 1988.
Kurabavashi et al., "Preparation of novel oxetane, etc.", CA115: 136655t (1991).
Antimicrobial Agents and Ghemotherapy, May 1989, pp. 773–775.
The Journal of Antibiotics, vol. 17, No. 4, pp. 644–646.
XXIX Interscience Conference on antimicrobial Agents and Chemotherapy 17–20 Sep. 1989, "Biochemical Activity of the New Antiviral SQ 32,829".
XXIX *Interscience Conference on Antimicrobial Agents and Chemotherapy*, 17–20 Sep. 1989, "In vitro Activity on SQ-32, 829, A New Nucleoside-Analog Antiviral Agent".
XXIX *Interscience Conference on Antimicrobial Agents and Chemotherapy*, 17–20 Sep., 1989, "Efficacy of SQ 33,054 [($\pm$)–BHCG] in Herpes Virus Infections in Mice".
Shimada, et al., Journal of Antibiotics vol. 39, No. 11, 1986 pp. 1623–1625.
Niitsuma, et al., Tetrahedron Letters, vol. 28, No. 34, pp. 3967–3970 (08/87).
Zemlicka, Nucleosides & Nucleotides, vol. 3(3), pp. 245–251, 262–264 (1984).
Hoshino, et al., J. Antibiot, 1987, vol. 40(7), pp. 1077–8 (07/87).
Shimada, et al., J. Antibiot., 1987, vol. 40 (12), pp. 1788–80 (12/87).
Niitsuma, et al., Chemical Abstracts, vol. 109: 38158q(1988).
Norbeck, et al., J. Am. Chem. Soc., vol. 110(21), pp. 7217–7218(10/88).

OXETANOCINS

CROSS-REFERENCE TO RELATED APPLICATION

This is a continuation-in-part of application Ser. No. 194,419 filed on May 13, 1988, now abandoned.

BACKGROUND OF THE INVENTION

This invention relates to novel oxetanocins exhibiting physiological activities such as immunosuppressive activity, antiviral activity, and the like.

As immunosuppressive agents, alkylating agents, antimetabolites, antibiotics, steroidal agents, folic acid antagonists, and vegetable alkaloids have hitherto been known. On the other hand, oxetanocin (OXT-A) itself is disclosed in Journal of Antibiotics, Vol. 39, No. 11, pp. 1623-25 (1986) and Japanese Patent Application Kokai (Laid-Open) No. 61-293,992 (EP No. 0 182 315).

Among the prior immunosuppressive agents, steroidal agents are said to exhibit their immunosuppressive action owing to their anti-inflammatory action and lympholytic action. Because of their diverse action, their use is accompanied by various side reactions, as is well known. It is also known that the other immunosuppressive agents belong to the so-called cytotoxic substances. Thus, it is desired to develop an agent selectively exercising its activity only on immunocomponent cells and exhibiting side reactions as mild as possible.

SUMMARY OF THE INVENTION

In view of the above, the present inventors conducted many studies to find that novel oxetanocins represented by the following general formula (I):

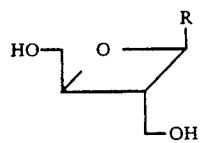

wherein R represents a group represented by

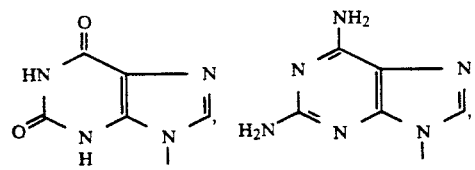

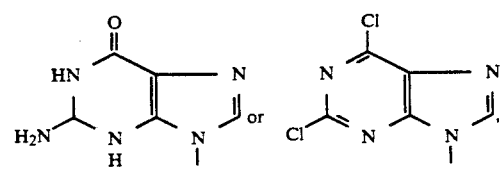

and their pharmacologically acceptable salts have immunosuppressive and antiviral activities. Based on this finding, this invention was accomplished.

Accordingly, this invention provides novel oxetanocins represented by the above-mentioned general formula (I) and their pharmacologically acceptable salts which are useful as a medical drug.

Further, this invention also provides an immunosuppressive composition and an antiviral composition containing these compounds as the active ingredient.

Furthermore, this invention provides a method for treating a disease caused by DNA virus in a warm-blood animal including human.

DETAILED DESCRIPTION OF THE INVENTION

Examples of the compound of this invention represented by general formula (I) are as follows:

| Abbreviation of compound | R in general formula (I) | Name of base R |
|---|---|---|
| OXT-X | | Xanthine |
| 2-Amino-OXT-A | | 2,6-Diaminopurine |
| OXT-G | | Guanine |
| OXT-DCP | | 2,6-Dichloropurine |

The oxetanocins of this invention can be produced by transforming the base part of oxetanocins by microbial, chemical and enzymatic methods.

Further, novel oxetanocins represented by the following general formula (II):

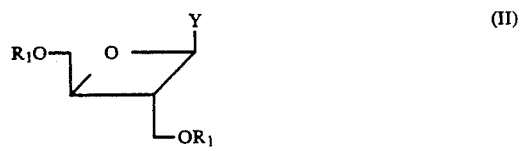

wherein Y represents

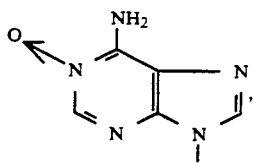

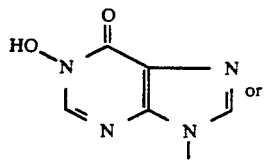

or

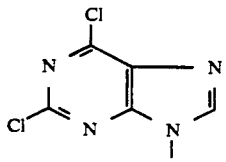

and $R_1$ represents a hydrogen atom, an acyl group or an optionally substituted lower alkyl group, provided that when Y is 2,6-dichloropurine, $R_1$ represents a group other than hydrogen, are useful as synthetic intermediates of 2-amino-OXT-A and OXT-G.

Examples of the compound of general formula (II) are as follows:

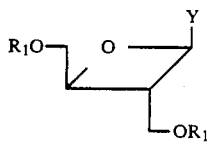
(II)

| Compound No. | $R_1$ | Y |
|---|---|---|
| Compound (5) | H | 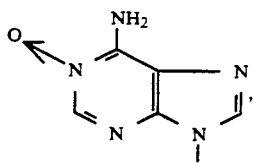 |
| Compound (6) | H | 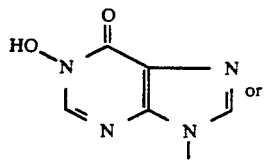 |
| Compound (8) | CH₃CO— | 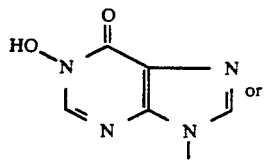 |

-continued

| Compound No. | $R_1$ | Y |
|---|---|---|
| Compound (9) | CH₃CO— | 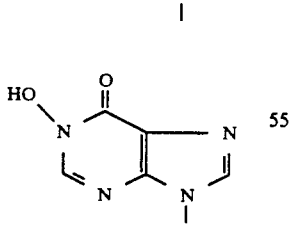 |

The compounds of this invention represented by general formulas (I) and (II) form salts with acids. The acid used for the salt formation may be any acid so far as it is pharmacologically acceptable, in the case of the compound of general formula (I). Examples of the acid preferably usable for this purpose include hydrochloric acid, sulfuric acid, phosphoric acid and the like. In the case of the compound of general formula (II), pharmacologically acceptable salts are of course usable, in addition to which salts with other various acids are also usable if such a salt is desirable.

Next, production processes of the compounds OXT-X, 2-amino-OXT-A and OXT-G will be described briefly.

(A) Production Process of Compound OXT-X:

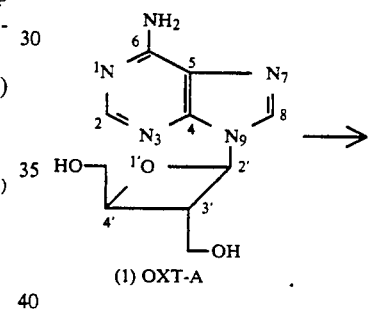
(1) OXT-A

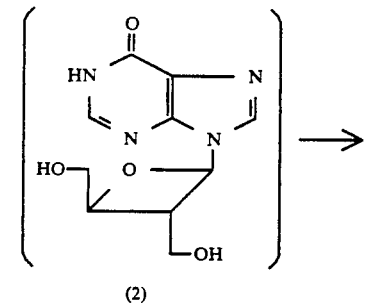
(2)

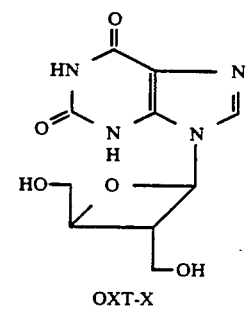
OXT-X

According to the above-mentioned scheme, oxetanocin (1) having adenine base is treated with an enxyme which oxidizes OXT-A to OXT-X, which is not limited to a purified enzyme, for example a cultured product of a microorganism having an ability to produce the enzyme or a treated product thereof (for example the crushed mycelium and cell free extract) or a substance collected from animal tissue (for example, rat liver homogenate) containing the same enzyme, in buffer solution of pH about 6 to 9, preferably about 7 to about 8 at about 10° C. to about 70° C. preferably about 20° C. to about 50° C., whereby novel compound OXT-X can be obtained according to the above-mentioned scheme.

When an enzyme originated from a microorganism is used, a cultured product (microbial cell) obtained by culturing a known microorganism having an ability to produce the said enzyme in a nutrient medium may be used as it is. Apart from it, acetone-dried microbial cell, crushed microbial cell, ultrasonic wave-treated microbial cell, crude enzyme sample collected from surfactant-treated, toluene-treated or lysozyme-treated microbial cell and microbial cell immobilized on natural or synthetic polymer are also usable in the same manner as above. In this reaction, isolation and purification of compound (2) is unnecessary. That is, the reaction can be carried out consecutively from compound (1) to OXT-X.

Concretely saying, the following microorganisms can be used, for example.

TABLE 1

| Name of microorganism | Deposit No. |
|---|---|
| Streptomyces alboniger[1] | IFO 12738 |
| Streptomyces californicus[1] | IFO 12750 |
| Streptomyces chrestomyceticus[1] | IFO 13444 |
| Streptomyces subsp. lasaliensis[2] | ATCC 31180 |
| Streptomyces albus[2] | ATCC 21838 |
| Streptomyces bikiniensis[1] | IFO 13198 |
| Streptomyces chrysomallus[1] | FO 12755 |
| Streptomyces olivaceus[1] | IFO 12805 |
| Streptomyces griseolus[1] | IFO 12777 |
| Nocardia interforma (M4-C5)[2] | ATTC 21072 |

Note:
[1] Anybody can freely obtain these microorganism for an experiment from Institute For Fermentation, Osaka (IFO): 17-85, Juso-honmachi 2-chome, Yodogawa-ku, Osaka 532, Japan.
[2] Anybody can freely obtain these microorganism for an experiment from American Type Culture Collection (ATCC): 12301 Parklawn Drive Rockville, MD 20852 U.S.A.

The production of OXT-X in this invention will be explained more concretely below. After culturing the microorganism shown in Table 1 in a nutrient medium for 40 hours, the cultured product may be used as it is. Preferably, however, the alive microbial cell is collected by centrifugation, made into a suspension in M/20 phosphate buffer (pH 7.5), mixed with compound (1) and reacted at 20° C. to 50° C. for 10 to 70 hours, whereby the intended compound OXT-X is formed in the reaction mixture. The product can be taken out of the reaction mixture by any known means. For example, after removing the cell body by centrifugation or the like, the product can be taken out by utilizing the difference in water or organic solvent. Otherwise, adsorption and desorption using active charcoal, adsorbent resin, ion exchange resin and the like can also be utilized. By appropriately combining these methods, the product can be taken out.

For example, compound (1) is converted to OXT-X by the action of a washed microbial cell listed in Table 1, and then inert substances and waste cells are removed by centrifugation.

The supernatant thus obtained is passed through an active charcoal column to have the product adsorbed on said column, after which the column is washed with water, the product is eluted with aqueous methanol and the eluted matter is concentrated to dryness to obtain a crude product. The latter is treated with a cation exchange resin and the adsorbed product is eluted with water and concentrated to dryness, whereby compound OXT-X is obtained in the form of a colorless powdery product.

(B) Production Process of 2-Amino-OXT-A:

2-Amino-OXT-A is prepared by reacting a compound represented by the following general formula:

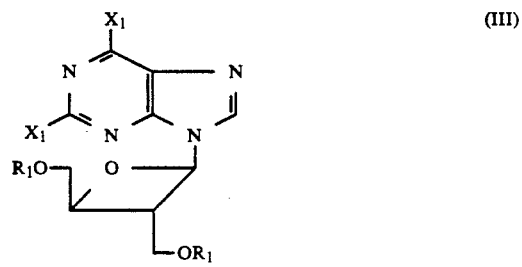

(III)

wherein $X_1$ represents a protected hydroxy group or a halogen atom and $R_1$ represents a protecting group, with ammonia in the presence of an inert solvent, usually a polar solvent such as a lower alcohol (for example ethanol) at a temperature of about 0° C. to about 200° C., usually about 20° C. to about 150° C., preferably about 70° C. to about 130° C.

The compound of the general formula (III) is prepared from OXT-X or OXT-A. That is, the compound [compound (4)] which is $X_1$ = protected hydroxy in the general formula (III) can be derived from OXT-X and the compound [compound (5)] which is $X_1$ = halogen in the general formula (III) is derived from OXT-A.

① OXT-X → 2-amino OXT-A

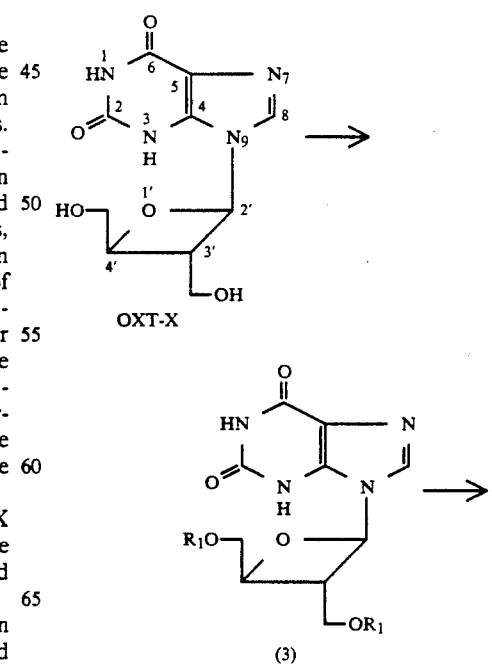

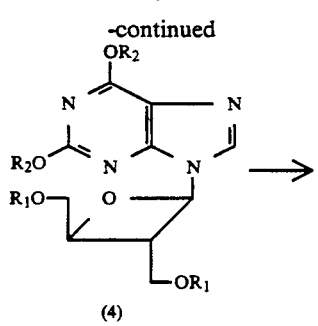

(4)

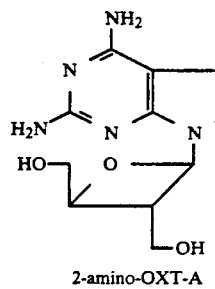

2-amino-OXT-A (In the formulas, R₁ and R₂ represent protecting groups.)

2-Amino-OXT-A having 2,6-diaminopurine base is produced by blocking the hydroxyl groups of 3'—CH$_2$OH and 4'—CH$_2$OH of OXT-X with some protecting group and blocking the 2- and 6-carbonyl groups of the base part of compound (3) and then subjecting compound (4) to an ammonolysis.

As the protecting group (R₁) for the hydroxyl group in compound (3), the known protecting groups for hydroxyl group used in the field of nucleic acid chemistry or sugar chemistry are used. Examples of the protecting group for the hydroxyl group of 3'—CH$_2$OH and 4'—CH$_2$OH include the following as follows:

(a) acyl groups such as ① formyl, ② optionally substituted-lower-alkylcarbonyls (as the substituent, halogen atom, lower alkoxy, benzoyl and the like can be referred to), for example, acetyl, chloroacetyl, trichloroacetyl, trifluoroacetyl, methoxyacetyl, pivaloyl, α- or β-benzoylpropionyl, phenoxyacetyl, trityloxyacetyl and the like); ③ benzoyl which may have substituents and (b) lower (C₁-C₆) alkyl groups preferably ① α-branched lower alkyl such as t-butyl and ② a lower alkyl groups substituted by phenyl an α-carbon such as trityl groups (trityl, trityl substituted by lower alkoxys, halogens or nitros such as monomethoxytrityl, dimethoxytrityl, trimethoxytrityl, and monohalogenotrityl, mononitrotrityl).

The above-mentioned protecting group can be introduced according to known methods. Preferably, a protecting group which is can be effectively eliminated afterwards should be chosen.

As the protecting group (R₂) for carbonyl group in compound (4), known protecting groups used in the field of nucleic acid chemistry are used. Examples of the protecting group for 2- and 6-carbonyl groups include an arylsulfonyl such as benzenesulfonyl which may have substituents on the phenyl moiety, for example, p-toluenesulfonyl, 2,4,6-triisopropylbenzenesulfonyl. These protecting groups can be introduced according to the known method. Preferably, a protecting group which can be easily substituted afterwards upon introduction of amino group into 2- and 6-positions should be chosen.

In producing 2-amino-OXT-A, compound (4) is subjected to ammonolysis. The ammonolysis can be performed by the known procedure. That is, compound (4) is dissolved into an anhydrous organic solvent and reacted with liquid ammonia.

② OXT-A→2-amino-OXT-A

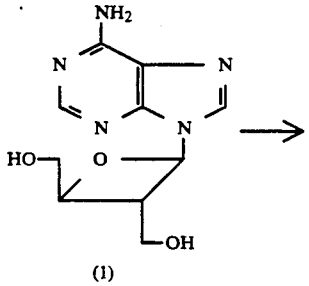

(1)

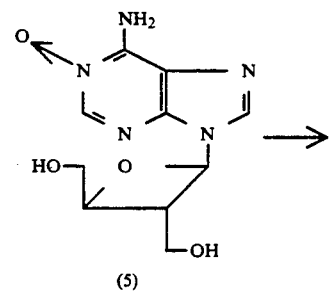

(5)

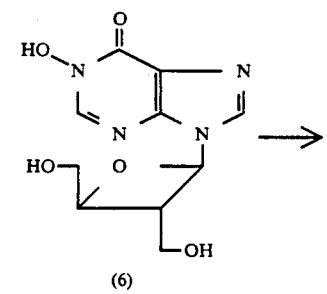

(6)

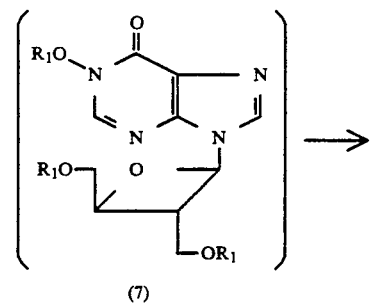

(7)

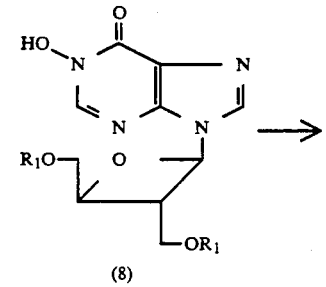

(8)

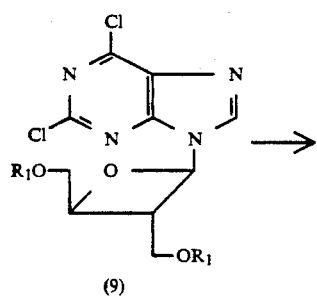

(9)

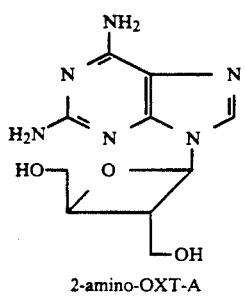

2-amino-OXT-A

In the first step, compound (1) is converted to N-oxide (5). This reaction is carried out with an appropriate oxidant. As said oxidant, hydrogen peroxide or organic peracid such as metachloro-perbenzoic acid, peracetic acid and the like is used. The reaction is usually carried out in an appropriate solvent, and examples of said solvent include optionally hydrated acetic acid, acetone, dioxane and the like. The reaction usually progresses at room temperature. N-Oxide (5) can be obtained from the reaction mixture by distilling off the solvent and purifying the residue by silica gel column chromatography.

In the next step, N-oxide (5) is treated with sodium nitrite to form compound (6).

This reaction is usually carried out in water at room temperature. Compound (6) can be isolated from the reaction mixture by concentrating the reaction mixture and purifying the product by column chromatography using a cation exchange resin. As the protecting group ($R_1$) for the hydroxyl group in compound (8), acyl group such as acetyl, chloroacetyl, pivaloyl, benzoyl and the like or trityl group such as trityl, monomethoxytrityl and the like is used. The protecting group can be introduced according to known procedure. Preferably, a protecting group which/can be effectively eliminated afterwards should be chosen. The reaction usually progresses at room temperature. Compound (7) can be isolated from the reaction mixture by distilling off the solvent and purifying the product by silica gel column chromatography.

Subsequently, compound (7) is dissolved into aqueous methanol and stirred at 20° C. to 70° C. for several days, whereby compound (8) is deposited in the form of a colorless powdery product. It is collected by filtration to obtain compound (8).

The compound (8) thus obtained is then chlorinated with freshly distilled phosphorus oxychloride in the presence of an appropriate organic base. As said organic base, triethylamine, pyridine, 2-picoline and the like can be used.

The reaction is usually carried out with heating. Compound (9) can be isolated from the reaction mixture by concentrating the reaction mixture under reduced pressure, dissolving the concentrate into an appropriate organic solvent and shaking it with a saturated aqueous solution of sodium hydrogen carbonate. As said organic solvent, chloroform, ethyl acetate and the like can be used. The organic layer is washed with a saturated aqueous solution of sodium chloride, the organic layer is concentrated, and the product is purified by silica gel column chromatography.

Subsequently, compound (9) is aminated to obtain 2-amino-OXT-A. This reaction is carried out by dissolving compound (9) into an appropriate anhydrous organic solvent and adding liquid ammonia thereto.

As said organic solvent, hydrocarbon solvents and their derivatives' preferably polar solvents (e.g. lower alcohols such as methanol, ethanol and the like, aliphatic nitriles such as acetonitrile and the like), etc. can be used. The reaction is carried out at a temperature of about 0° C. to about 200° C., usually at about 20° C. to about 150° C. and preferably at about 70° C. to about 130° C. The reaction time is about one hour to about 100 hours. 2-Amino-OXT-A can be isolated from the reaction mixture by distilling off the solvent and purifying the product by column chromatography using an adsorbent resin.

(C) Production Process of OXT-G:

2-Amino-OXT-A→OXT-G

Compound OXT-G can be produced by treating 2-amino-OXT-A with adenosine deaminase in water or aqueous solution. As for the adenosine deaminase, a pure or crude enzyme or a substance including an adenosine deaminase such as a cultured microorganism including adenosine deaminase, its treated product, or a substance including adenosine deaminase collected from animal tissue such as bovine intestinal mucosa are used. As the adnosine deaminase, commercial products may be used. As a concrete example of the commercial product, EC,3,5,4,4 manufactured by Sigma Co. can be referred to.

When an enzyme originated from microorganism is used, a cultured product of microorganism (microbial cell) prepared by culturing a microorganism having adenosine deaminase-producing ability in a nutrient medium can be used as it is.

Concretely saying, the microorganisms shown in Table 2 can be used, for example.

TABLE 2

| Name of microorganism | Deposit No. |
|---|---|
| Alcaligenes bookeri[1] | IFO 12948 |
| Escherichia coli NIHJ[3] | NIHJ |
| Proteus morganii[1] | IFO 3168 |
| Elytrosporanim brasiliense[1] | IFO 1259 |
| Nocardia asteroides[1] | IFO 3423 |
| Streptomyces alboniger[1] | IFO 12738 |
| Streptomyces californicus[1] | IFO 12750 |
| Streptomyces chrestomyceticus[1] | IFO 13444 |
| Streptomyces subsp. lasaliensis[2] | ATCC 31180 |
| Streptomyces tubercidicus[1] | IFO 13090 |
| Streptomyces verticillus[2] | ATCC 31307 |
| Aspergillus niger[1] | IFO 4066 |
| Fusarium roseum[1] | IFO 7189 |

[1]These microorganisms can be freely obtained from IFO.
[2]These microorganisms can be freely obtained from ATCC.
[3]These microorganisms can be freely obtained from National Institute of Health of Japan (NIHJ); 2-10-35, Kamiosaki, Shinagawa-ku, Tokyo, Japan.

In producing OXT-G, 2-amino-OXT-A are treated with an adenosine deaminase in 1/20M–1/5M phosphate or tris-HCl buffer, pH about 6 to about 10 (preferable pH about 7.0 to about 8), at a temperature of about 10° C. to about 90° C., usually at about 20° C. to about 25° C., for a period of about 0.5 hour to about 200 hours, usually for about 10 hours to about 60 hours, whereby the intended compound OXT-G is formed in the reaction mixture. When a cultured microorganism is used, the microorganism shown in Table 2 is cultured in a nutrient medium for 24 hours. Although the cultured product may be used as it is, more preferably the alive microbial cell is collected by centrifugation, suspended into M/20 phosphate buffer (pH about 7.0 to about 8.0), mixed with 2-amino-OXT-A and reacted usually at about 20° C. to about 70° C. for at most about 200 hours, whereby the intended compound OXT-G is formed in the reaction mixture. The product can be isolated from the reaction mixture according to known procedure. That is, a method which comprises removing inert material by centrifugation or the like and taking out the product by utilizing the difference in solubility into water or organic solvent, the method of adsorption-desorption using active charcoal, adsorbent resin or ion exchange resin, and the like can be adopted in appropriate combinations.

For example, after reacting 2-amino-OXT-A with the above-mentioned enzyme or washed microbial cell shown in Table 2, inert materials or waste microbial cells are removed by centrifugation. The supernatant is passed through a column of porous resin to have the product adsorbed thereon. After washing the column with water, the product is eluted with aqueous methanol and concentrated to dryness, whereby OXT-G is obtained in the form of a colorless powdery product.

If necessary, Sephadex resins are also usable in this procedure.

When the compound of general formula (I) is used as a medical drug such as immunosuppressive agent, antiviral agent or the like, it is administered in the form of injection, oral composition, suppository and the like either alone or in mixture with diluent or vehicle. As said vehicle or diluent, pharmacologically acceptable ones are chosen, and their kind and composition vary dependent on the route and method of administration. Although the content of the compound of this invention in the prepared pharmaceutical composition varies with the type of composition, it is usually about 0.05% to about 100% by weight and preferably about 1% to about 90% by weight of the total weight of the composition. For example, in the case of injection, it is usually preferable to adjust the content of the compound of this invention to usually about 0.5% to about 10% preferably about 0.1% to about 5% by weight of the total weight. For oral administration, the compound of this invention is used together with the above-mentioned solid or liquid carrier in the form of tablet, capsule, powder, granule, liquid, dry syrup or the like. In case of capsule, tablet, granule and powder, the content of the compound of this invention is about 3% to about 100% by weight and preferably 5% to 90% by weight of the total weight, and the remainder is carrier.

The dose is dependent on the age, body weight and symptoms of the patient and the purpose of the therapy. Usually, it is 1 to 300 mg/kg.day in non-oral administration and 5 to 500 mg/kg.day in oral administration.

The compound of this invention is characterized by its low toxicity. Further, all the compounds of this invention are characterized by the small accumulation of toxicity after a continued administration.

In forming the compound of this invention into a pharmaceutical composition, it is treated in the following manner, for example. Thus, 30 parts by weight of hydrochloride of the compound of general formula (I) is dissolved into purified water so as to give a total quantity of 2,000 parts. The resulting solution is sterilized by filtration by the use of Millipore Filter type GS.

Two grams of the filtrate is taken into a vial and freeze-dried. Thus, a freeze-dried injection containing 30 mg of hydrochloride of the compound of general formula (I) per one vial is obtained.

In the similar method to Waithe et al. (Waithe et al., Handbook of Experimental Immunology, 26, 1, 1978), compounds OXT-X, 2-amino-OXT-A and OXT-G were examined for the effect on lymphocyte blastgenesis. As the result, compounds OXT-X, 2-amino-OXT-A and OXT-G markedly suppressed the blastgenesis of T lymphocyte stimulated by Con A (concanavalin A) and the blastgenesis of B lymphocyte stimulated by LPS (lipopolysaccharide).

This means that the compounds of this invention OXT-X, 2-amino-OXT-A and OXT-G inhibit the function of B lymphocyte and T lymphocyte. Since this inhibitory action means inhibition of humoral immunity and cell-mediated immunity, respectively, the immunosuppressant comprising the compound of this invention as active ingredient is quite useful for inhibiting the refusal reaction in the transplantation of organs and skins, for treating various self-immune diseases such as multiple sclerosis, hemolytic anemia, I type diabetes mellitus, heavy myasthenia, Hashimoto thyroiditis, Behcet syndrome and rheumatism, and for treating allergic diseases. Since the compound of this invention is considered different from prior immunosuppressants in the action mechanism, it is considered free from the severe side reactions such as disorder in hematopoietic tissues generally recognized in cytotoxin type suppressants and the gastric ulcer, cataract, etc. recognized in steroid hormones. Thus, the compound of this invention is quite excellent in the point of side reaction.

Next, the pharmacological activity of the compound of this invention will be concretely explained with reference to test examples.

Test Example 1:

Inhibition of T lymphocyte blastgenesis caused by Con A:

Spleen cells of BALB/©  mouse were dividingly poured into microplate at a rate of $2 \times 10^5$ cells/0.2 ml/well. Test compounds of varied concentration were added to wells other than control group. Further, Con A was added to all the wells at a rate of 5 micrograms/ml. Then, the cell suspensions were cultured at 37° C. for 72 hours in a culture chamber having an atmosphere of 5% v/v carbon dioxide. The extent of lymphocyte blastgenesis was determined by adding 1 μci/well of $^3$[H]-thymidine 6 hours before completion of culture and measuring the intake into cultured cells by means of a liquid scintillation counter. Numerical value (1-B dpm/A dpm)×100 was taken as inhibitory rate of each sample compound on blastgenesis, wherein A dpm was intake count in the case of adding Con A only and B dpm was intake count in the case of adding Con A and the sample compound. The results are shown in Table 3.

TABLE 3

Inhibitory activities of OXT-X, 2-amino-OXT-A and OXT-G on the T lymphocyte blastgenesis caused by Con A

| Name of compound | OXT-X | | | 2-Amino-OXT-A | | | OXT-G | | |
|---|---|---|---|---|---|---|---|---|---|
| Concentration ($\mu$g/ml) | 0.8 | 4.0 | 20.0 | 0.8 | 4.0 | 20.0 | 0.8 | 4.0 | 20.0 |
| Inhibitory rate (%) | 11 | 36 | 71 | 21 | 94 | 99 | 85 | 96 | 100 | control (no sample) 0%

As is apparent from Table 3, the compound of this invention inhibits the T lymphocyte blastgenesis to a great extent.

Test Example 2:

Inhibition of B lymphocyte blastgenesis caused by LPS (lipopolysaccharide)

According to the method of Test Example 1 (except that 100 $\mu$g/ml of Escherichia coli LPS was added in place of Con A), the intake of $^3$[H]-thymidine into blastgenesis B cells was measured. The inhibitory rate of the test sample was similarly determined.

As shown in Table 4, the compound of this invention inhibits the blastgenesis of B lymphocyte caused by LPS to a great extent.

TABLE 4

Inhibitory actions of OXT-X, 2-amino-OXT-A and OXT-G on the blastgenesis of lymphocyte caused by LPS

| Name of compound | OXT-X | | 2-Amino-OXT-A | | OXT-G | |
|---|---|---|---|---|---|---|
| Concentration ($\mu$g/ml) | 4.0 | 20.0 | 4.0 | 20.0 | 4.0 | 20.0 |
| Inhibitory rate (%) | 8.0 | 27.0 | 23.0 | 93.0 | 64.0 | 93.0 |

Control (no sample) 0%

The compound of this invention exhibits its activity against viruses. The viruses are (a) DNA virus' for example ① pox virus, ② herpes virus such as herpes sinplex virus (HSV), cytomegalovirus, ③ adenovirus, ④ papovavirus, ⑤ hepatitis B virus, ⑥ parvovirus, etc.; and (b) RNA virus' for example ① rhabdovirus, ② paramyxovirus, ③ arenavirus, ④ retovirus which cause AIDS or human T cell leukemia etc., ⑤ coronavirus, ⑥ Bunyavirus, ⑦ togavirus, ⑧ picornavirus, ⑨ reovirus, Epstein-Barr virus, etc. Thus, it is useful as an antiviral agent and is expected to be effective as a therapeutic drug for various viral diseases such as herpes, AIDS, B hepatitis and the like.

Next, the antiviral activity of the compound of this invention will be concretely explained with reference to test examples.

Test Example 3

(1) Test in vitro (a) Anti-herpes virus activity

A microplate having 96 wells was used. A medium containing a predetermined quantity of a compound of this invention and 5 to 10 TCID$_{50}$ of herpes type II (HSV-II) were added on a single layer of Vero cell and cultured at 37° C. for 96 to 120 hours in 5% (v/v) carbon dioxide incubator, after which the cytopathic effect (CPE) of HSV-II on the Vero cells was visually examined under microscope to determine the antiviral activity. The antiviral activity was expressed by 50% inhibitory concentration ($\mu$g/well) on CPE. The results are shown in Table 5.

TABLE 5

| | Antiviral activity (HSV-II) |
|---|---|
| Compound | 50% CPE-inhibitory concentration ($\mu$g/well) |
| OXT-X | 107.5 |
| OXT-G | 9.7 |
| 2-Amino OXT-A | 17.6 |

The results of comparative test are as shown in Table 6.

TABLE 6

| | Antiviral activity (HSV-II) |
|---|---|
| Compound | (ED$_{50}$, $\mu$g/ml) |
| Control | |
| OXT-A | 10 |
| OXT-H | >50 |
| Present invention | |
| OXT-G | 2.2 |
| 2-Amino OXT-A | 4.2 |

(b) Anti-HIV (human immunodeficiency virus) activity

MT-4 cell (about 100,000 cells/ml) was added into a 24 well tray, and then 100 microliters of a solution containing a predetermined quantity of a compound of this invention was added. After culturing it at 37° C. for 5 hours in 5% (v/v) carbon dioxide incubator, $10^3$ to $10^4$ infection units of HIV was added and cultured for 4 days. Then, a part of the culture fluid was coated onto a slide glass and immobilized with acetone, after which development of virus antigen was observed by indirect fluorescent antibody method.

As the primary antibody of the fluorescent antibody method, a serum of AIDS patient was used. As its secondary antibody, FITC-labelled human IgG was used.

Cell denaturation of MT-4 cells by the compound of this invention was carried out without adding virus, and it was visually examined under microscope. The results are shown in Table 7.

TABLE 7

Anti-HIV activity of the compounds of this invention

| Compound | OXT-X | | | 2-Amino-OXT-A | | | OXT-G | | |
|---|---|---|---|---|---|---|---|---|---|
| Concentration ($\mu$g/ml) | 1 | 10 | 100 | 1 | 10 | 100 | 1 | 10 | 100 |
| Cell denaturation | − | − | ±~+ | − | − | ±~+ | − | − | +++ |
| Development of virus antigen (%) | 66 | 52 | 5 | 30 | 26 | 5 | 42 | 17 | |

Note:
The compound of this invention was used in the form of a solution in dimethylaulfoxide (DMSO). In a run using DMSO only, the development of virus antigen was 80 to 90%.

As is apparent from Table 7, the compound of this invention exhibits a remarkable growth-inhibitory activity on HIV with only a small extent of cell denaturation. Accordingly, the compounds of this invention are expected to be effectively usable as a therapeutic drug for AIDS.

(c) Anti-cytomegalovirus activity

Anti-cytomegalovirus activity was determined in the following manner. Thus, a 35 mm$\phi$ dish containing a single layer of human fetal fibroblasts was infected with 100 PFU (plaque forming units) of cytomegalovirus (A01169 strain). After absorption for one hour, a medium containing a varied concentration of the compound of this invention (0.5% agarose, 2% fetal calf serum) was superposed thereon, and the whole was cultured at 37° C. for 10 days in 5% (v/v) carbon dioxide incubator, after which the formation of plague was measured. The results are shown in Table 8 in terms of 50% inhibitory value ($IC_{50}$).

TABLE 8

| Compound name | Anti-cytomegalovirus activity $IC_{50}$ (μg/ml) |
| --- | --- |
| Control | |
| OXT-A | 13 |
| OXT-H | 18 |
| Present invention | |
| OXT-G | 1 |
| 2-Amino-OXT-A | 2 |

As is apparent from Table 8, the compounds of this invention have an anti-cytomegalovirus activity, and OXT-G and 2-amino-OXT-A are particularly outstanding in the inhibitory action.

(d) Hepatitis B virus inhibitory activity

According to Dulbecco, a cultured liver cell strain HB 611 producing and releasing active hepatitis B virus [Proc. Natl. Acad. Sci. USA, 84 (1987), p.444] was cultured at 37° C. in modified Eagle medium (GIBCO) in the presence of 10% fetal calf serum, 200 micrograms/ml of G418, 100 u/ml of Penicillin and 100 u/ml of Streptomycin with 5% carbon dioxide. It was inoculated into a 6-well plate at a rate of $5 \times 10^4$ cells/well (35 mmφ). When 50% confluent was reached in one or two days, a predetermined quantity of the compound of this invention was added and the culture was continued. Thereafter, the medium was exchanged with a fresh medium containing the same test chemical at the same concentration at intervals of every 3 days, and the culture was continued for 15 days in the total. Then, the medium was removed, and the cell was treated with 0.5 ml of lysis buffer (10 mM Tris-HCl, pH 7.8/5 mM $Na_2EDTA$, 1% SDS/0.1 mg/ml Pronase K) at 37° C. for one hour to obtain a solution. The DNA thus obtained was purified by RN-ase treatment, phenol-chloroform treatment, and ethanol precipitation method. Then, 5 micrograms of DNA was subjected to Hind III treatment, and DNA pattern was analyzed by southern blot method by using $^{32}$p-labelled hepatitis B virus DNA as a probe. The results are shown in Table 9.

TABLE 9

| | Anti-hepatitis B virus activity of the compounds of this invention | | |
| --- | --- | --- | --- |
| Compound name | Concentration (μg/ml) | Virus DNA synthesis inhibitory effect | Cytotoxicity |
| OXT-H | 50 | + | − |
| | 20 | − | − |
| | 5 | − | − |
| OXT-G | 100 | +++ | − |
| | 50 | +++ | − |
| | 20 | +++ | − |
| | 10 | +++ | − |
| | 5 | +++ | − |
| | 2 | + | − |
| 2-Amino-OXT-A | 100 | +++ | + |
| | 50 | +++ | − |
| | 20 | +++ | − |

TABLE 9-continued

| | Anti-hepatitis B virus activity of the compounds of this invention | | |
| --- | --- | --- | --- |
| Compound name | Concentration (μg/ml) | Virus DNA synthesis inhibitory effect | Cytotoxicity |
| | 10 | +++ | − |
| | 5 | + | − |
| | 2 | + | − |
| Control | 0 | − | − |

(2) Test in vivo (a) Effect of treatment with OXTs against HSV-2 infection in mice The 8-week old male ICR mice were inoculated intraperitoneally (ip) with herpes simplex virus type-2(HSV-2)strain 186 at $2.5 \times 10^5$ PFU/0.2 ml/mouse. OXTs were administered ip once a day with the indicated doses for 5 days, starting 6 hours after inoculation. The survival rates (%)of mice treated with OXTs were evaluated at least for 3 weeks after inoculation. The results obtained are as shown in Table 10.

TABLE 10

| OXTs | Dose mg/kg/day | Survivor/Total (%) |
| --- | --- | --- |
| OXT-G | 5 | 3/10 (30) |
| | 10 | 8/10 (80) |
| | 20 | 10/10 (100) |
| 2-Amino-OXT-A | 10 | 7/10 (70) |
| Control | 0 | 0/10 (0) |

As shown in Table 10, OXTs were found to be highly effectively against the systemic HSV-2 infection.

(b) Efficacy of treatment with OXT-G against MCMV infection in mice

The 4-week old male ICR mice was inoculated intraperitoneally with Smith strain of murine cytomegalovirus (MCMV) at $1 \times 10^5$ PFU/0.2 ml and treated with 10 mg/kg/day of OXT-G once a day for 5 days, starting 6 hours after inoculation. The mortality and changes in body weight were monitored every day. The results obtained are as shown in Table 11.

TABLE 11

| | Efficacy of treatment with OXT-G on the body weight of MCMV-infected mice | | | | |
| --- | --- | --- | --- | --- | --- |
| | Dose mg/kg/day | Average (5 mice) of body weight (g) (days) | | | |
| | | 0 | 4 | 8 | 14 |
| OXT-G | 10 | 18.0 | 20.0 | 24.5 | 31.0 |
| Control[1] | 0 | 18.0 | 17.0 | 18.0 | 26.5 |
| Control[2] | 0 | 18.0 | 27.5 | 31.0 | 35.0 |

Control[1]: Two mice died at 5 days from inoculation.
Control[2]: Not inoculated with MCMV.

As shown in Table 11, the mice receiving OXT-G at dose of 10 mg/kg/day maintained their body weight on the initial level for several days and gradually gained weight thereafter.

Titers of MCMV in various tisues of the mice were examined and the results were shown in Table 12.

TABLE 12

Titers of MCMV in various tissues of mice treated or untreated with OXT-G.

| Organs | Virus titer[1] (PFU/0.1 g tissue) 6 days after infection | | | |
|---|---|---|---|---|
| | Nontreated | | OXT-G-treated[2] | |
| Spleen | 5.1 | 4.9 | <2 | <2 |
| Liver | 4.4 | 2.8 | <2 | <2 |
| Kidney | 3.7 | 3.4 | <2 | <2 |
| Lung | 4.0 | 2.8 | <2 | <2 |

As shown in Table 12, MCMV was recovered from all the tissues examined of untreated mice. OXT-G treated mice showed a significant reduction in the quantity of MCMV recovered from the tissues.

(c) Efficacy of OXT-G and 2-Amino-OXT-A against DHBV-infected Duck

Newborn ducklings were intraperitoneally infected with 50 μl of duck hepatitis B virus (DHBV) containing sera. Persistent infection in ducks was confirmed by dot-blot hybridization of sera taken from 6 week old ducks. Ducks were intraperitoneally treated with the indicated doses of OXT-G and 2-Animo-OXT-A once a day for 6 days. After treatment of OXTs sera were collected and examined for the presence of DHBV-DNA by dot-blot hybridization as $^{32}$p-labeled DHBV DNA probe. The results obtained are as shown in Table 13.

TABLE 13

| OXTs | Dose mg/kg/day | Content (%) of DHBV in sera |
|---|---|---|
| OXT-G | 20 | 9 |
| | 50 | 25 |
| | 100 | 3 |
| 2-Amino-OXT-A | 20 | 28 |
| | 50 | 18 |
| | 100 | 8 |
| Control | 0 | 100 |

As shown in Table 13, OXTs given intraperitoneally once a day at 20-100 mg/kg rapidly cleared DHBV-DNA from the sera of persistently infected ducklings. OXTs showed strong inhibition of DHBV replication.

As is apparent from the result of test Example 3, the compounds of this invention, especially, OXT-G and 2-amino-OXT-A are useful for treating a disease caused by DNA viruses such as HSV-II, HCMV and HBV in warm-blooded animal.

In the case of administration of the compound to said animal suffering from the said disease, the dosage is determined depending on the age, body weight and symptom of the animal as well as the purpose of treatment. The therapeutic dose generally ranges from 1 to 300 mg/kg.day for parenteral administration, and from 5 to 500 mg/kg.day for oral administration.

The compound is slightly toxic, and every derivative of it is characterized by low cumulative toxicity by repetitive administration. Any toxic sign has not been observed after 1 administration of dose of 800 mg/kg of the Compound for intraperitoneal administration in mice.

EXAMPLE 1

(Production of Compound OXT-X)

After pouring 100 ml portions of a medium consisting of 98% of water, 1% of yeast powder and 1% of dextrose (pH 7.0) into 500 ml Erlenmeyer flasks, the contents of the flask were sterilized in an autoclave at 120° C. for 20 minutes.

One platinum loop quantity of Nocardia interforma M4-C5 (ATCC No. 21072) (obtained from ATCC) was inoculated into each flask and subjected to an aerobic shaking culture at 28° C. for 48 hours. Apart from it, 100 ml portions of a medium having the same composition as above was poured into 500 ml Erlenmeyer flasks and sterilized at 120° C. for 20 minutes. Then, 2 ml of the above-mentioned culture fluid in the first flask was transplanted into each of the second flasks and subjected to shaking culture at 28° C. for 40 hours.

Subsequently, 11.7 liters of the culture fluid thus obtained was centrifuged at 6,500 r.p.m. for 12 minutes. The collected alive microbial cell was washed with two 500 ml portions of M/20 phosphate buffer (pH 7.5) and then suspended into 5.4 liters of the same buffer as above. One hundred milliliter portions of the suspension thus obtained were dividingly poured into 60 Erlenmeyer flasks having a capacity of 500 ml. To each of the flasks, a solution of 2 mg/ml of compound (1) (OXT-A) in 10 ml of M/20 phosphate buffer was added and shaken at 37° C. for 18 hours, after which the cell body was centrifuged out under the same condition as above. The resulting supernatant was passed through a column packed with 300 ml of active charcoal powder (chromatography grade, manufactured by Wako Junyaku K.K.) to have the product adsorbed on the column. After washing the column with water, the product was eluted with 2.1 liters of 50% aqueous methanol, and the eluted solution was concentrated to dryness to obtain 1.4 g of OXT-X in the form of a yellowish powder. The crude powder thus obtained was dissolved into 50 ml of water and passed through a column packed with 90 ml of Dowex ® 50 W×4 (H-form, ion exchange resin, 50 to 100 mesh). The adsorbed product was eluted with 1.5 liters of water and concentrated to dryness. Thus, 1.02 g (yield 79.6%) of compound OXT-X was obtained as a colorless powder.

FD-MS; 269 (M+H)+

UV; $\lambda^{pH8.0}_{max}$ (log ε) 250.5 nm (4.01), 276.5 nm (3.95) NMR (400 MHz, D$_2$O) δppm; 3.67-3.94 (5H, m, 3'-H, 3'—CH$_2$OH, 4'—CH$_2$OH), 4.72 (1H, m, 4'-H), 6.28 (1H, d, 2'-H), 7.84 (1H, s, 8-H) OXT-X can obtain by the similar method to this example other than using a microorganism listed in Table 14 instead of Nocardia interforma M4-C5 in the example.

TABLE 14

| Name of microorganism | Deposit No. | Convertion* rate (%) |
|---|---|---|
| Streptomyces aboniger[1] | IFO 12738 | 79.6 |
| Streptomyces californicus[1] | IFO 12750 | 59.9 |
| Streptomyces chrestomyceticus[1] | IFO 13444 | 70.0 |
| Streptomyces subsp. lasaliensis[2] | ATCC 31180 | 59.0 |
| Streptomyces albus[2] | ATCC 21838 | 100 |
| Streptomyces bikiniensis[1] | IFO 13198 | 80.9 |
| Streptomyces chrysomallus[1] | IFO 12755 | 17.9 |
| Streptomyces olivaceus[1] | IFO 12805 | 41.9 |
| Streptomyces griseolus | IFO 12777 | 100 |

*Note: Convertion rate of OXT-A to OXT-X.

EXAMPLE 2

[Production of Compound (3) R$_1$=—COCH$_3$)]

To a suspension of 1.02 g of compound OXT-X in 50 ml acetonitrile were successively added 1.06 ml of triethylamine, 11.6 mg of 4-dimethylaminopyridine and 0.72 ml of acetic anhydride. The resulting mixture was stirred at room temperature for 4 hours. After concentrating the reaction mixture under reduced pressure, the concentrate was dissolved into 5 ml of chloroform-methanol (9:1) mixture and passed through a column of 40 g silica gel (Art 7734, manufactured by Merck Co.), and the adsorbed product was eluted successively with 500 ml of chloroform-methanol (9:1) and 800 ml of chloroform-methanol (85:15). Then, it was subjected to silica gel (Art 5715, manufactured by Merck) thin layer chromatography (developer: chloroform-methanol 3:1), and the fractions having Rf value of about 0.2 were collected and concentrated to dryness under reduced pressure. Thus, 1.21 g (yield 90%) of compound (3) was obtained.

FD-MS; 352 (M+)

NMR (60 MHz, CD$_3$OD) δppm; 2.08

(3H, s, —CH$_2$—O—C(=O)—CH$_3$), 2.17(3H, s, —CH$_2$—O—C(=O)—CH$_3$), 3.82(1H, m, 3'-H), 4.39(4H, m, 3'-CH$_2$—O—C(=O)—CH$_3$,

4'-CH$_2$—O—C(=O)—CH$_3$), 4.65–4.71 (1H, m, 4'—H), 6.34 (1H, d, 2'—H), 8.10 (1H, s 8—H)

EXAMPLE 3

[Production of Compound (4)

(R$_1$ = —COCH$_3$,

R$_2$ = —SO$_2$—[2,4,6-triisopropylphenyl with CH(CH$_3$)$_2$ groups])]

To a solution of 1.34 g of compound (3) in 45 ml of methylene chloride were successively added 4.24 ml of triethylamine, 23.2 mg of 4-dimethylaminopyridine and 4.61 g of 2,4,6-triisopropylbenzenesulfonyl chloride in this order. The resulting mixture was stirred at room temperature for 3 hours.

The reaction mixture was concentrated under reduced pressure to dryness, the concentrate was dissolved into 15 ml of chloroform and passed through a column of 120 g of silica gel, and the adsorbed matter was eluted with chloroform. Then, it was subjected to silica gel (Art 5715, manufactured by Merck) thin layer chromatography and developed with ether. The fractions having Rf value of about 0.41 were collected and concentrated to dryness under reduced pressure to obtain 2.65 g (yield 78.7%) of compound (4) as a powdery product.

FAB-MS; 885 (M+H)+

NMR (60 MHz, CDCl$_3$) δppm; 1.14–1.32 (36H, m,

—CH(CH$_3$)(CH$_3$) × 6), 2.09(3H, s, —COCH$_3$), 2.12(3H, s, —COCH$_3$), 2.92(2H, m, —CH(CH$_3$)(CH$_3$) × 2), 3.72–4.46 (9H, m), 4.64–4.86 (1H, m, 4'—H), 6.33 (1H, d, 2'—H), 7.18 (4H, m), 8.41 (1H, s, 8—H)

EXAMPLE 4

[Production ① of 2-Amino-OXT-A]

Into 16 ml of anhydrous ethanol was dissolved 2.65 g of the compound (4) obtained in Example 3. About 50 ml of liquid ammonia was added to the solution, and the resulting mixture was stirred in a sealed tube at 105° C. for 57 hours.

After removing the ammonia, 100 ml of water was added, the insoluble matter was removed, and the filtrate was treated with 300 ml of MCI ® GEL CHP20P (high polous stylene-divinylbenzene copolymer) (Mitsubishi Chemical Industry Co., Ltd.) to have the product adsorbed thereon. After washing the resin with water, the adsorbed matter was eluted by the linear concentration gradient method using 1,200 ml of water and 1,200 ml of 50% aqueous methanol. It was subjected to silica gel (Art 5715, manufactured by Merck) thin layer chromatography, using chloroform-methanol (2:1) as developer. Fractions having Rf value of about 0.44 were collected and concentrated to dryness under reduced pressure to obtain 445 mg (yield 55.8%) of 2-amino-OXT-A as a powdery product.

FD-MS; 266 (M+)

UV; λ$^{H_2O}$ $_{max}$ (log ε) 256 nm (3.96), 278 nm (3.95)

NMR (400 MHz, D$_2$O) δppm; 3.68–3.91 (5H, m), 4.68 (1H, m), 6.25 (1H, d), 8.13 (1H, s)

EXAMPLE 5

[Production ② of 2-Amino-OXT-A]

(a) Production of Compound (5)

Into a mixture consisting of 18 ml of water and 60 ml of dioxane were dissolved 808 mg of compound (1) and 748 mg of m-chloroperbenzoic acid, and the resulting solution was stirred in a dark room at room temperature for 18 hours. The reaction mixture was concentrated to dryness under reduced pressure, and the residue was interspersed on 6 grams of silica gel and added to a 45 g column of the same silica gel as above. Then, it was eluted with 200 ml of chloroform-methanol (10:1), 200 ml of chloroform-methanol (5:1) and 500 ml of chloroform-methanol (3:1), successively. Then, the eluted matter was subjected to silica gel thin layer chromatography using chloroform-methanol 2:1) as a developer, and fractions having Rf value of about 0.18 were collected and concentrated to dryness under reduced pressure to obtain 721 mg (yield 83.9%) of compound (5).

FAB-MS; 268 (M+H)+

UV; λ$^{H_2O}$$_{max}$ 233, 262, 295 nm

NMR (60 MHz, D$_2$O) δppm; 3.99–4.30 (5H, m), 4.70 (1H, m), 6.71 (1H, d), 8.73 (1H, s), 8.87 (1H, s)

(b) Production of Compound (6)

Into a mixture consisting of 1.6 ml of water and 0.6 ml of acetic acid was dissolved 110 mg of compound (5). Then, 276 mg of sodium nitrite was added thereto, and resulting mixture was stirred at room temperature for 3 days.

The reaction mixture was concentrated under reduced pressure, the concentrate was passed through a 4 ml column of Dowex ® 50W×8 (H-form), and it was eluted with water. The eluted matter was subjected to silica gel thin layer chromatography using n-butanol-acetic acid-water (3:1:2) as a developer. The fractions having Rf value of about 0.08 were collected and concentrated under reduced pressure to dryness. Thus, 58.6 mg (yield 53.3%) of compound (6) was obtained.

FAB-MS; 269 (M+H)+

UV; $\lambda^{0.1N\ NaOH}_{max}$ 256, 294 nm

NMR (60 MHz, D$_2$O) δppm; 3.70–4.30 (5H, m), 4.61 (1H, m), 6.60 (1H, d), 8.60 (1H, s), 8.67 (1H, s)

(c) Production of Compound (8) (R$_1$=—COCH$_3$)

To a suspension of 206 mg of compound (6) in 10 ml acetonitrile were successively added 0.315 ml of triethylamine, 10 mg of 4-dimethylaminopyridine and 0.25 ml of acetic anhydride. The resulting mixture was stirred at room temperature for 18 hours. The reaction mixture was concentrated to dryness under reduced pressure, and the residue was dissolved into chloroform, passed through a 30 g silica gel column, and eluted successively with 200 ml of chloroform-methanol (30:1) and then 300 ml of chloroform-methanol (5:1). Then, the eluted matter was subjected to silica gel thin layer chromatography using chloroform-methanol (10:1). Fractions having Rf value of about 0.55 were collected and concentrated to dryness under reduced pressure to obtain compound (7). It was dissolved into 20 ml of methanol-water (5:1) and stirred at 43° C. for 2 days. The resulting colorless powdery precipitate was collected by filtration to obtain 198 mg (yield 74%) of compound (8).

FAB-MS; 353 (M+H)+

UV; $\lambda^{MeOH}_{max}$ 245, 251, 270 nm

NMR (60 MHz, CD$_3$OD) δppm; 2.10 (3H, s), 2.13 (3H, s), around 4.46 (5H, m), 6.43 (1H, d), 8.33 (1H, s), 8.43 (1H, s)

(d) Production of Compound (9) (R$_1$=—COCH$_3$)

Into a mixture consisting of 1 ml of phosphorus oxychloride and 0.3 ml of triethylamine was suspended 53 mg of compound (8) obtained in the same manner as in Example 7, and the suspension was heated under reflux for 20 minutes. The reaction mixture was concentrated to dryness under reduced pressure, and the residue was shaken with 20 ml of chloroform and 20 ml of saturated aqueous solution of sodium hydrogen carbonate. The organic layer was washed with 10 ml of saturated aqueous solution of sodium chloride, dehydrated with anhydrous sodium sulfate and evaporated to dryness under reduced pressure. The residue was passed through a 15 g silica gel column and eluted with 200 ml of chloroform-methanol (30:1). The eluted matter was subjected to silica gel thin layer chromatography, using chloroform-methanol (10:1). Fractions having Rf value of about 0.56 were collected and concentrated to dryness under reduced pressure to obtain 13.6 mg (yield 23.2%) of compound (9).

FD-MS; 388 (M+)

UV; $\lambda^{MeOH}_{max}$ 252, 273 nm

NMR (60 MHz, CD$_3$OD) δppm; 2.08 (6H, s), around 4.47 (5H, m), 6.57 (1H, d), 8.83 (1H, s)

(e) Production of 2-Amino-OXT-A

Compound (9) (27 mg) obtained in the same manner as in Example 8 was suspended into 12 ml of ethanol, to which was added 15 ml of liquid ammonia. The mixture was stirred in a sealed tube at 110° C. for 72 hours.

After removing the ammonia, the reaction mixture was concentrated to dryness under reduced pressure. The residue was dissolved into water, passed through a 20 ml column of MCI ® GEL CHP20P and eluted by linear concentration gradient method using 80 ml of water and 80 ml of 50% aqueous methanol.

The eluted matter was subjected to silica gel thin layer chromatography using chloroform-methanol (2:1) as a developer. Fractions having Rf value of about 0.44 were collected and concentrated to dryness under reduced pressure to obtain 13.1 mg (yield 71.3%) of 2-amino-OXT-A as a colorless powdery product.

FD-MS; 266 (M+)

UV; $\lambda^{H_2O}_{max}$(log ε) 256 nm (3.96), 278 nm (3.95)

NMR (400 MHz, D$_2$O) δppm; 3.68–3.91 (5H, m), 4.68 (1H, m), 6.25 (1H, d), 8.13 (1H, s)

EXAMPLE 6

(Production of OXT-G)

One hundred microliters (100 units) of adenosine deaminase (EC 3.5.4.4, manufactured by Sigma Co.) was added to a solution of 240 mg of 2-amino-OXT-A in 150 ml of M/10 phosphate buffer (pH 7.5), and the mixture was stirred at 22° C. for 41 hours.

The reaction mixture was treated with 100 ml of MCI ® GEL CHP20P, and the adsorbed substance was eluted with water.

The eluted matter was subjected to silica gel thin layer chromatography using n-butanol-acetic acid-water (4:1:2) as a developer. Fractions having Rf value of about 0.42 were collected and concentrated to dryness under reduced pressure to obtain 240 mg (yield 99.6%) of compound OXT-G as a colorless powder.

FD-MS; 268 (M+H)+

UV; $\lambda^{pH6.0}_{max}$(log ε) 253.5 nm (4.09)

NMR (400 MHz, D$_2$O) ppm; 3.69–3.87 (5H, m), 4.66–4.69 (1H, m), 6.29 (1H, d), 8.17 (1H, s)

EXAMPLE 7

(Production of OXT-G)

One hundred milliliter portions of a medium (pH 7.0) containing 0.3% of meat extract, 1.0% of peptone and 0.7% of sodium chloride were dividingly poured into 500 ml Erlenmeyer flasks and sterilized in an autoclave at 120° C. for 20 minutes. Each flask was inoculated with one platinum loop quantity of Escherichia coli NIHJ and subjected to an aerobic shaking culture at 37° C. for 18 hours. Then, 1,000 ml of the culture fluid was centrifuged at 10,000 r.p.m. for 10 minutes to collect the alive microbial cell. After washing it three times with an equal quantity of M/20 phosphate buffer (pH 7.0), it was suspended into 100 ml of the same buffer solution as above. Then, 50 mg of 2-amino-OXT-A was added to the suspension and reacted at 37° C. for 18 hours with shaking, after which the reaction mixture was heated at 100° C. for 5 minutes to stop the reaction. The microbial cells were removed by centrifugation, and the supernatant was passed through a column packed with 50 ml of MCI Gel ® CHP20P to have the product adsorbed thereon. After washing the column with water, the adsorbed matter was eluted with 150 ml of 20% aqueous methanol and concentrated to dryness. Thus, 45.1 mg (yield 90.0%) of OXT-G was obtained as a colorless powder.

EXAMPLE 8

(Production of OXT-DCP)

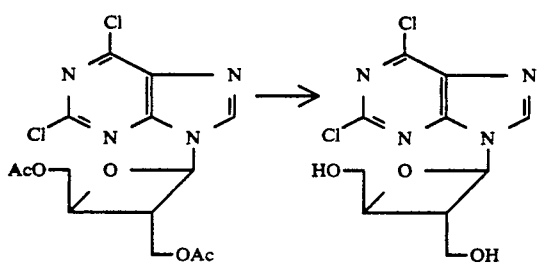

Compound (9) (6.3 mg) obtained in Example 6 (d) was dissolved into 1 ml of methanol, to which was added 0.04 ml of 1N aqueous solution of ammonia. After stirring the mixture at room temperature for 2 hours, 0.04 ml of 1N hydrochloric acid was added thereto. The reaction mixture was concentrated to dryness under reduced pressure, the residue was dissolved into water and passed through a 10 ml column of MCI® GEL CHP20P, the column was washed with water and the adsorbed matter was eluted with 80% aqueous methanol. The eluted substance was subjected to silica gel thin layer chromatography using chloroform-methanol (10:1) as a developer. Fractions having Rf value of about 0.35 were collected and concentrated to dryness under reduced pressure to obtain 4.4 mg (yield 91%) of compound (2) as a colorless powder.

UV; $\lambda^{MeOH}_{max}$ 252, 273 nm

FAB-MS; 304 (M+)

NMR (400 MHz, CD$_3$OD) δppm; 3.72–3.93 (5H, m), 4.69 (1H, m), 6.33 (1H, d), 8.89 (1H, s)

What is claimed is:

1. An oxetanocin of the following formula (I) and pharmacologically acceptable salts thereof:

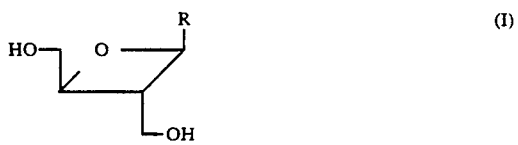 (I)

wherein R is a group represented by

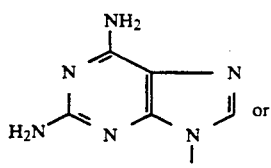

(2-Amino-OXT-A)

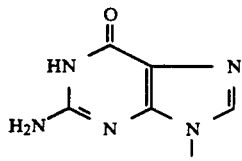

(OXT-G)

2. An oxetanocin of the following formula:

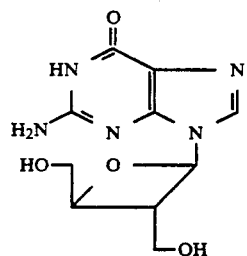 (OXT-G)

and pharmacologically acceptable salts thereof.

3. A method for treating a disease caused by DNA virus in a warm-blooded animal which comprises administering an oxetanocin represented by the following general formula (I) and pharmacologically acceptable salts thereof:

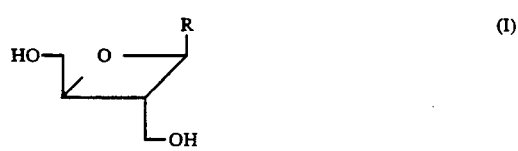 (I)

wherein R is a group represented by

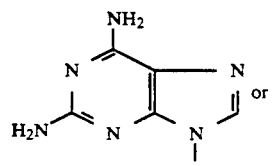

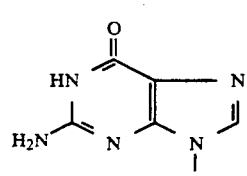

in an effective amount to the said warm-blooded animal.

4. A compound of the following formula

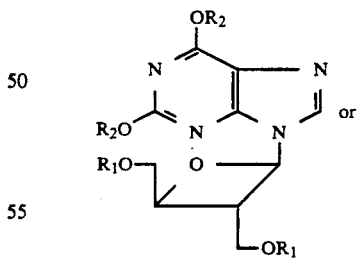

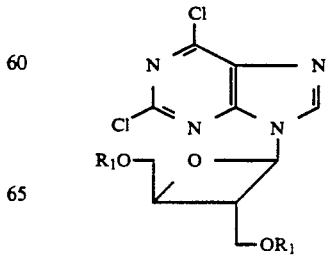

wherein $R_1$ and $R_2$ each represents a protective group of hydroxy group.

5. A method for treating a disease caused by DNA virus in a warm-blooded animal in accordance with claim 3, wherein said DNA virus is hepatitis B virus.

6. A method for treating a disease caused by DNA virus in a warm-blooded animal in accordance with claim 3, wherein said DNA virus is cytomegalovirus.

7. A method for treating a disease caused by DNA virus in accordance with claim 3, wherein said virus is hepatitis B or cytomegalovirus, and wherein said oxetanocin comprises OXT-G.

* * * * *